United States Patent [19]
Ohara et al.

[11] Patent Number: 5,601,418
[45] Date of Patent: Feb. 11, 1997

[54] BLOOD PUMP

[75] Inventors: Yasuhisa Ohara; Kenzo Makinouchi; Yukihiko Nosé, all of Houston, Tex.

[73] Assignees: Kyocera Corporation, Kyoto, Japan; Baylor College of Medicine, Houston, Tex.

[21] Appl. No.: 488,719

[22] Filed: Jun. 8, 1995

Related U.S. Application Data

[63] Continuation of Ser. No. 55,233, Apr. 28, 1993, abandoned.

[51] Int. Cl.[6] .............................. F04B 17/00; F04B 15/02
[52] U.S. Cl. ................. 417/420; 417/424.2; 417/423.12; 415/900; 384/907.1
[58] Field of Search ............................ 417/420, 423.12, 417/423.14, 424.1, 424.2; 415/900, 203, 218.1, 219.1; 384/907.1, 243, 246

[56] References Cited

U.S. PATENT DOCUMENTS

| | | | |
|---|---|---|---|
| 3,932,069 | 12/1974 | Giardini et al. | 417/420 |
| 4,507,048 | 3/1985 | Belenger et al. | 415/90 X |
| 4,541,786 | 9/1985 | McLean | 417/407 |
| 4,824,262 | 4/1989 | Ramingaito et al. | 384/907.1 |
| 5,253,986 | 10/1993 | Bond et al. | 417/420 |
| 5,399,074 | 3/1995 | Nosé et al. | 415/900 |

Primary Examiner—John J. Vrablik
Assistant Examiner—William Wicker
Attorney, Agent, or Firm—Loeb & Loeb LLP

[57] ABSTRACT

A centrifugal blood pump for heart-lung machines or the like. An impeller is provided with pump vanes and a magnet. The impeller is rotatably accommodated in a casing having an inlet and an outlet. A magnet drive means is disposed outside the casing. The impeller is supported by at least three balls above a bottom plate of the casing, held at the center of the bottom plate and rotated around the center axis of the impeller by the magnet means and the magnet drive means. When the upper and lower ends of the rotation shaft of the impeller are supported by the casing, the upper end of the rotation shaft is supported by a bearing embeddedly disposed at the top section of the conical section of the casing, and the inlet of the casing is disposed adjacent to and eccentric from the top section.

8 Claims, 15 Drawing Sheets

BLOOD PUMP

This is a continuation of application Ser. No. 08/055,233 filed on Apr. 28, 1993, now abandoned.

BACKGROUND OF THE INVENTION

1. Field of the Invention

The present invention relates to a centrifugal blood pump used for heart-lung machines or the like.

2. Prior Arts

In recent years, centrifugal blood pumps have begun to be used widely as blood circulation pumps for heart-lung machines or the like. In the case of a centrifugal blood pump having a structure wherein the rotation shaft of the impeller with pump vanes accommodated in the casing thereof passes through the casing, however, thrombus is apt to occur at bearings and sealing parts because of blood stagnation around the rotary sealing parts for sealing the rotation shaft of the impeller and heat generation in the rotary sealing parts. Furthermore, there is the danger of leaking blood because of incomplete operation or deterioration of the rotary sealing parts during use. By reason of these problems, such a centrifugal blood pump has a disadvantage of being incapable of operating continuously for an extended period of time.

To solve these problems, various centrifugal blood pumps have been developed, which require no sealing parts at the rotation shaft thereof. As a pump with no sealing parts, a centrifugal blood pump is known, wherein a conical impeller comprising pump vanes and a magnet means such as permanent magnets for rotating the impeller in cooperation with a magnet drive means is accommodated in the conical casing thereof having an inlet port and an outlet port, the upper and lower ends of the rotation center axis of the impeller are supported inside the casing and the impeller is rotated by a magnet drive means, such as electric coils, for generating a rotating magnetic field, disposed outside the casing, as disclosed by U.S. Pat. No. 4,507,048.

In this kind of a blood pump, a pivot is formed on the bottom end side of the rotation center axis line of the impeller thereof and this pivot is supported by a bearing, such as a watch-type jewelled bearing or the like, disposed at the central section of the upper surface of the casing's bottom wall. The shaft or pivot formed on the upper end side of the rotation center axis line of the impeller is supported by a bearing which is supported by an appropriate supporting means, such as a bar, spider or ring, just under the inlet port provided at the top section of the conical casing. In the case of the centrifugal blood pump disclosed by the above-mentioned USP, wherein both the pivots formed on the upper and lower end sides of the rotation center axis line of the impeller are supported by watch-type jewelled bearings, an adjusting means (a screw adjusting means for example) for adjusting the positional relationship between the bearing on the upper end side and the bearing on the lower end side, that is, the difference in height between the two bearings is provided.

When the pivot or shaft on the upper end side of the impeller rotation center axis line is supported by a mechanical bearing, such as a watch-type jewelled bearing as described above, it is found that the following problems are apt to occur.

Blood sucked from the inlet port collides against the bearing provided just under the inlet port positioned at the top section of the conical casing, the supporting means, such as a bar, spider or ring, for supporting the bearing, and the adjusting means for adjusting the positional relationship between the bearing on the upper end side and the bearing on the lower end side. The flow of the blood is thus disturbed by the collision, thereby causing the problem of damaged blood cells, that is, hemolysis and thrombus.

To avoid the generation of hemolysis and thrombus, the supporting means, such as a bar or the like, for supporting the bearing must be made as slender as possible. As a result, the supporting means may deform during pump operation. If such a deformation occurs, the distance between the upper and lower bearings, which was adjusted properly before operation, and the contact pressure between the impeller and the upper and lower pivots are changed, thereby hindering the impeller from rotating stably. This unstable rotation further increases the deformation of the supporting means, resulting in the breakage of the supporting means in an extreme case.

Accordingly, the above-mentioned centrifugal blood pump cannot be used continuously for an extended period of time because of the generation of hemolysis and thrombus and the unstable rotation of the impeller due to the deformation of the bearing supporting means during operation as described above.

SUMMARY OF THE INVENTION

The present invention is intended to solve the above-mentioned problems encountered in centrifugal blood pumps. An object of the present invention is to provide a centrifugal blood pump, wherein blood sucked from the inlet port of the casing thereof does not collide against bearings and supporting means for supporting the bearings, and the flow of the blood is not disturbed to prevent the generation of hemolysis and thrombus.

Another object of the present invention is to provide a centrifugal blood pump which decreases the danger of deforming a bearing supporting means or the like during operation and can be operated stably for an extended period of time.

Still another object of the present invention is to provide a centrifugal blood pump which scarcely causes hemolysis and thrombus during operation, ensures stable impeller rotation and is capable of operating for an extended period of time.

To achieve the above-mentioned objects, the blood pump of the present invention comprises a casing having an inlet port and an outlet port and rotatably accommodating an impeller, the impeller being of a nearly conical shape and provided with pump vanes on the side surface thereof and a magnet means for rotating the impeller on the bottom surface thereof, and a magnet drive means disposed opposite to the above-mentioned magnet means with the casing intervened therebetween for supporting the impeller at the center above the bottom plate of the casing and for rotating the impeller around the rotation center axis of the impeller in cooperation with the above-mentioned magnet means, wherein the impeller is rotatably supported by at least three balls above the bottom plate of the casing.

In addition, the blood pump of the present invention proposed to achieve the above-mentioned objects comprises a casing having an inlet port and an outlet port and rotatably accommodating an impeller, the impeller being provided with a magnet means for rotating the impeller and pump vanes on the side surface thereof, and a magnet drive means disposed opposite to the above-mentioned magnet means with the casing intervened therebetween for rotating the impeller around the rotation center axis of the impeller in cooperation with the above-mentioned magnet means, wherein the lower end of the rotation center axis of the above-mentioned impeller is supported by a bearing disposed on the bottom plate of the casing and the upper end of the above-mentioned rotation center axis is supported by a bearing directly disposed at the conical top section of the casing and the above-mentioned inlet port is disposed adjacent to and eccentric from the top section of the casing.

DETAILED DESCRIPTION OF THE INVENTION

Figure 1:
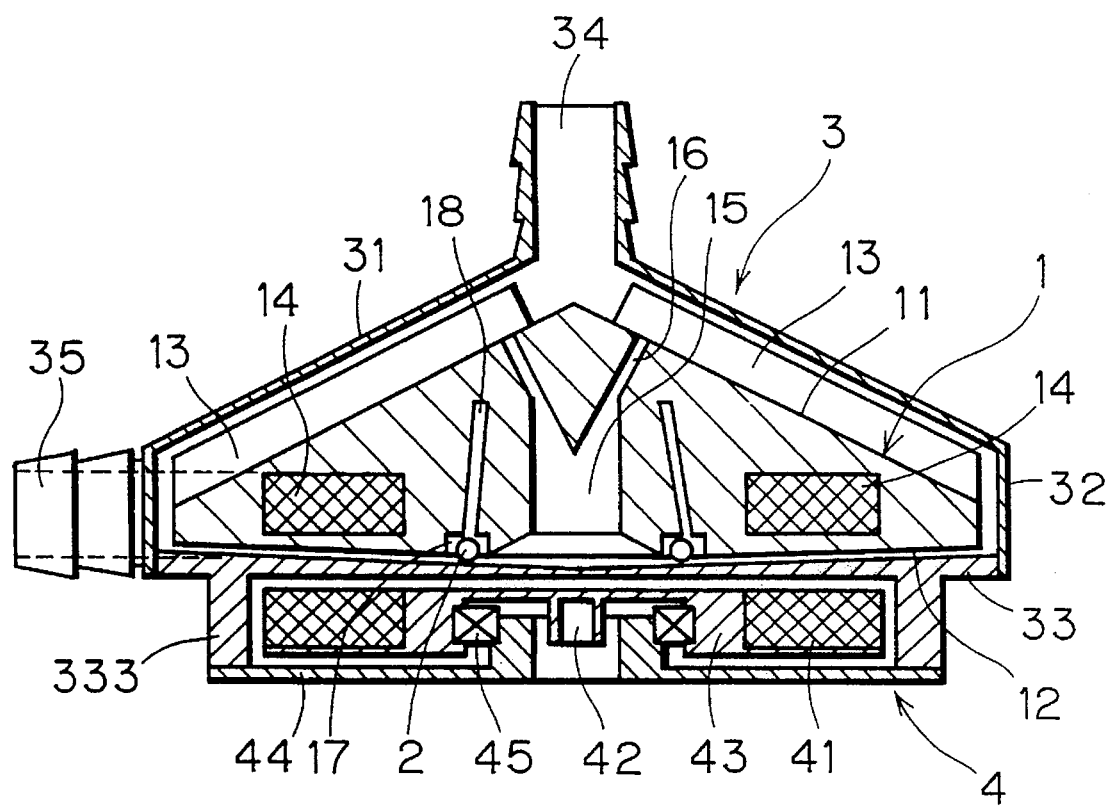
FIG. 1 is a vertical sectional view of an embodiment of the blood pump of the present invention.

To achieve the above-mentioned objects, the centrifugal blood pump of the present invention comprises a casing S having an inlet port 34 and an outlet port 35 and rotatably accommodating an impeller 1, the impeller 1 being of a nearly conical shape and provided with pump vanes 13 on the side surface thereof and permanent magnets 14 constituting a magnet means for rotating the impeller 1 on the bottom surface thereof, and a magnet drive means 4 disposed opposite to the above-mentioned permanent magnets 14 with the casing 3 intervened therebetween For supporting the impeller 1 at the center above the bottom plate 33 of the casing 3 and for rotating the impeller 1 around the rotation center axis thereof in cooperation with the above-mentioned permanent magnets, wherein the impeller 1 is rotatably supported by at least three balls 2 above the bottom plate 33 of the casing 3.

The balls 2 are preferably made of ceramics, metal or ceramic-coated metal, rotatably supported by ball supporting sections disposed on the bottom surface of the impeller or on the upper surface of the bottom plate of the casing. The balls move while rotating on the surface of a member disposed opposite to the ball supporting sections, that is, a ball receiving section. The impeller supported by the balls 2 above the bottom plate 33 is retained at the center above the bottom plate of the casing and rotated around the rotation center axis of the impeller by the cooperative operation of the above-mentioned magnet means and magnet drive means. The rotation of the impeller is thus smooth and stable. As described above, the impeller rotation shaft of the blood pump of the present invention is not supported by the casing. The blood pump, therefore, does not require any pivot, any pivot bearing or any bearing supporting means at the upper end of the impeller rotation shaft. Consequently, the blood sucked from the inlet port 34 of the casing 3 does not collide against such obstacles. The flow of the blood is, therefore, not disturbed by the obstacles, thereby preventing the generation of hemolysis and thrombus. In addition, another embodiment of the blood pump of the present invention being proposed to achieve the above-mentioned objects comprises a casing 3 having an inlet port 34 and an outlet port 35 and rotatably accommodating an impeller 1, the impeller 1 being provided with permanent magnets 14 constituting a magnet means for rotating the impeller and pump vanes 13 on the side surface thereof, and a magnet drive means 4 disposed opposite to the above-mentioned permanent magnets 14 with the casing 3 intervened therebetween for rotating the impeller 1 around the rotation center axis of the impeller 1 in cooperation with the above-mentioned permanent magnets 14, wherein the lower end of the rotation shaft 19 of the above-mentioned impeller 1 is supported by a bearing disposed on the bottom plate of the casing, the upper end of the above-mentioned rotation center axis is supported by bearing 24 disposed at the conical top section 311 of the casing 3, and the inlet port 34 of the casing 3 is disposed adjacent to and eccentric from the top section 311.

The inlet port 34 extends parallel to the center line of the conical section 31 and being eccentric from the top section 311 of the conical section 31 of the casing 3. In another case, the inlet port 34 extends in the direction inclined 90 degrees or less from the center line of the conical section and being eccentric from the top section 311 of the conical section 31 of the casing 3.

In the above-mentioned blood pump of the present invention, the upper end of the rotation shaft 19 of the impeller 1 is supported by the bearing 24 directly disposed at the top section 311 of the conical section 31 of the casing 3 and the inlet port 34 is disposed eccentric from the top section 311 as described above. For these reasons, the blood sucked from the inlet port 34 of the casing 3 does not directly collide against the upper end of the rotation shaft 19 or the bearing 24, and the flow of the blood is not disturbed by these obstacles, thereby preventing the generation of hemolysis and thrombus. Furthermore, since the upper and lower ends of the rotation shaft of the impeller 1 are supported by the bearings, the rotation of the impeller is smooth and stable.

DETAILED DESCRIPTION OF THE PREFERRED EMBODIMENT

Figure 2:
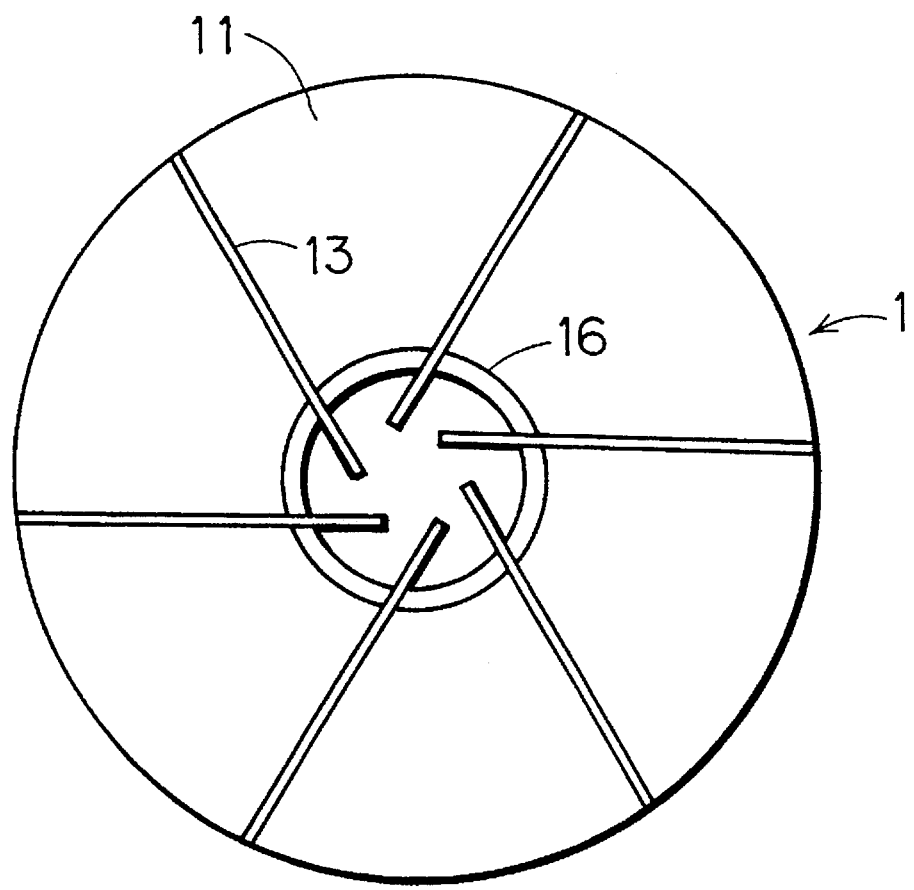
FIGS. 2 and 3 are top and bottom plan views respectively illustrating the impeller of the embodiment of the blood pump shown in FIG. 1.
Figure 3:
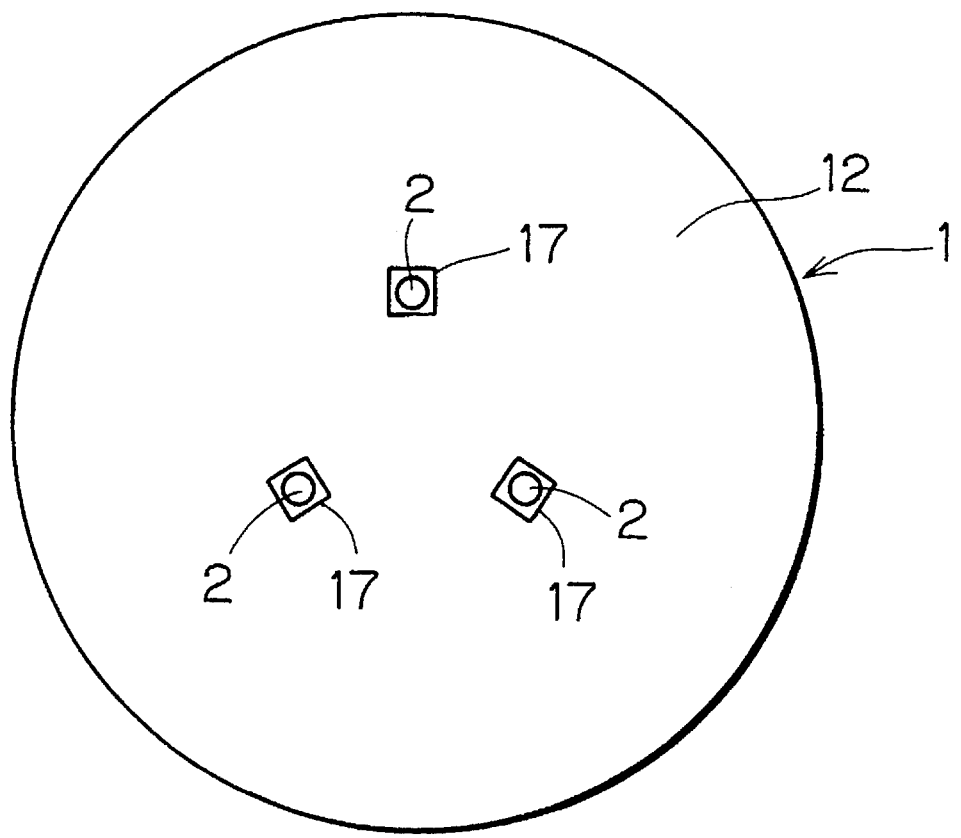

FIGS. 1 to 3 show an embodiment of the centrifugal blood pump of the present invention. Numeral 1 represents an impeller rotatably accommodated in a casing 3 and the impeller has a nearly conical shape. The impeller 1 is usually made of synthetic resin, such as polyethylene, polypropylene, polymethyl methacrylate or polycarbonate. On the side surface 11 of the conical impeller 1, pump vanes 13 are disposed. When the impeller rotates, the pump vanes 13 performs pumping, that is, feeds blood sucked from the inlet port 34 of the casing 3 to the outlet port 35 and discharges the blood from the outlet port 35. To prevent the rotatable pump vanes 13 of the impeller from being brought into direct contact with the casing 3 at the upper inner surface thereof, stopper projections can be interposed between the rotatable vanes 13. On the bottom surface 12 of the impeller 1. A group of permanent magnets 14, which function as a magnet means for rotating the impeller 1, are arranged symmetrically around the rotation center axis of the impeller, that is, the center axis of the conical section. In addition, the impeller 1 has a center stabilizing hole 15 with a diameter of 3 to 20 mm, being opened at the center of the bottom surface of the impeller 1 and extending along the rotation center axis of the impeller 1. The stabilizing hole 15 communicates with a blood passage 16 being opened around the top section of the conical section. When the impeller 1 rotates and the blood pressure on the upper side of the impeller 1 becomes lower than that on the lower side of the impeller 1 in the casing, a force to lift the impeller 1 is generated. The stabilizing hole 15 functions to reduce the lifting force by decreasing the pressure difference. The stabilizing hole 15 also functions to improve the flow of the blood at the bottom section of the impeller 1 where blood stagnation is apt to occur, thereby preventing the generation of thrombus at the bottom section.

Figure 4:
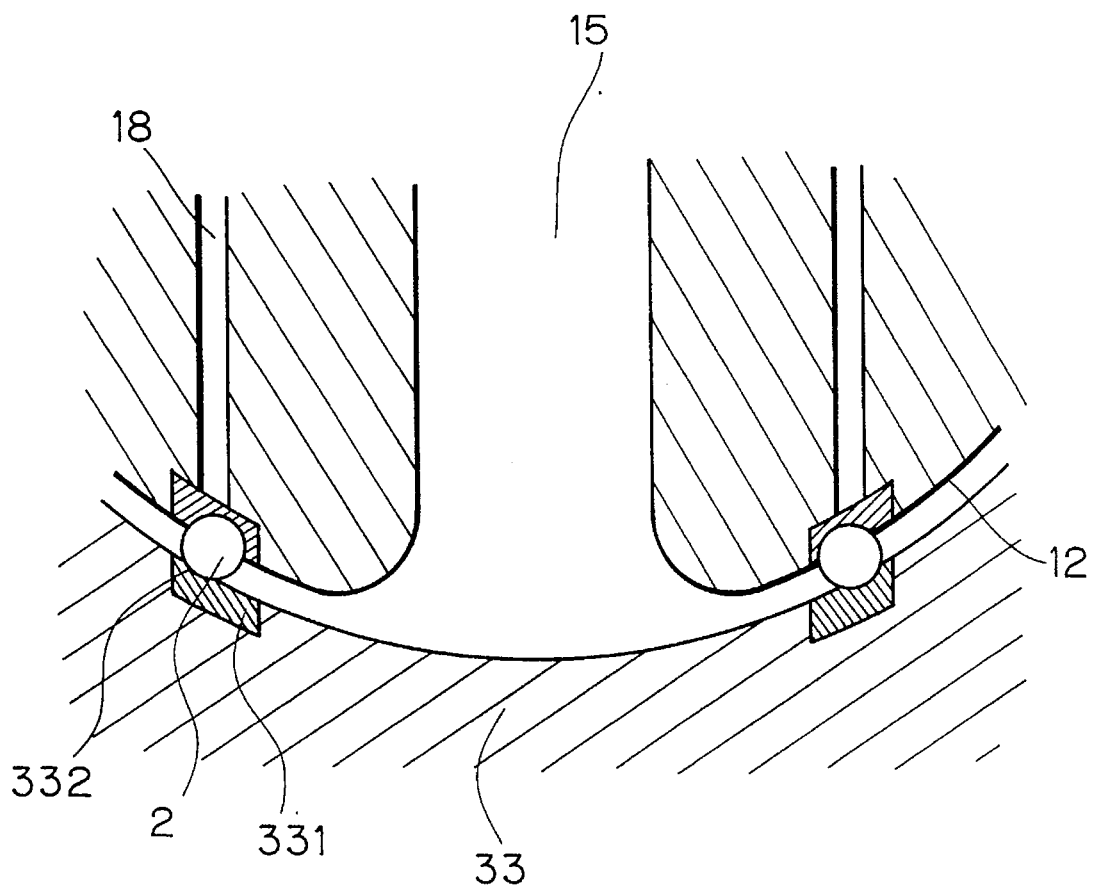
FIG. 4 is an enlarged sectional view of balls for supporting the impeller above the bottom plate of the casing, and ball supporting sections and a ball receiving section of the embodiment of the blood pump shown in FIG. 1.

On the bottom surface 12 of the impeller 1, at least three ball supporting sections 17 (three pieces are shown in FIG. 4) are formed 1 mm or more away from the center of the bottom surface symmetrically and equally spaced around the center. The ball supporting sections 17 are formed in a square shape as shown in FIG. 3 or a circular concave shape. Balls 2 are rotatably supported individually in the ball supporting sections 17. The balls 2 are removable from the ball supporting sections 17. However, in some cases, the ball supporting sections 17 can have a structure wherein the balls 2 are retained by the ball supporting sections 17 and cannot be removed. The balls 2 move around the rotation center axis of the impeller 1 while rotating the inner surface of the bottom plate 33 of the casing 3. In other words, the impeller 1 is rotatably supported around the rotation center axis of the impeller 1 above the inner surface of the bottom plate 33 of the casing 3 by at least three balls (three pieces are shown in FIG. 3). On the inner surface of the bottom plate 33, a ring-shaped ball receiving section 331, such as a track formed on the bottom plate 33 of the casing 3 as shown in FIG. 4 can also be provided. In this case, the balls 2 move while rotating on the ball receiving section 331. As shown in FIG. 4, a guide groove 332 can also be formed in the ball receiving section 331 along the rotation track for the balls 2. Moreover, the balls 2 can move while sliding on the ball receiving section 331 in the condition that the balls 2 are supported unrotatably. In this case, curved end projections (not shown) can be provided instead of the balls 2.

The balls 2 are preferably made of ceramics, such as alumina, silicon carbide or zirconia, being superior in resistance against thrombus and friction, or made of metal, such as a titanium alloy or a cobalt-chrome alloy. Furthermore, the balls 2 can be coated with ceramics, such as titanium nitride (TiN) or titanium carbide (TiC). The size of the balls 2 should preferably be as small as possible to reduce the generation of hemolysis and thrombus, but should preferably be as large as possible to increase the durability thereof. A proper size of the balls 2 is in the range of 1 to 10 mm in diameter. Moreover, the balls should preferably be positioned externally away from the center of the bottom surface to prevent the generation of thrombus and to stably support the impeller 1. As described above, the balls 2 should be positioned at least 1 mm or more away from the center of the bottom surface.

Although the ball supporting sections 17 for supporting the balls 2 can have a concave shape formed on the bottom surface of the impeller 1 made of synthetic resin, they should preferably comprise separate members made of one of the above-mentioned ceramics or metals, or a high polymer material different from that used for the impeller 1 as shown in FIG. 4. Both the casing 3 and the bottom plate 33 thereof are usually made of the same synthetic resin as that used for the impeller 1. Accordingly, the above-mentioned ball receiving section SSI can also be made of synthetic resin. However, like the ball supporting sections 17, the ball receiving section 331 should preferably comprise a separate member made of one of the above-mentioned ceramics or metals, or a ceramic-coated metal.

By forming tubular chambers 18 behind the ball supporting sections 17 on the bottom surface of the impeller 1, it is possible to fill anticoagulant in the tubular chambers 18. The anticoagulant is gradually discharged during pump operation and increases the concentration of the anticoagulant in the blood at the ball supporting sections 17, around the balls 2 and inside the stabilizing hole 15, thereby preventing the generation of thrombus at the ball supporting sections 17, around the balls 2 and inside the stabilizing hole 15.

Furthermore, for the purpose of preventing the generation of thrombus, the rotation of the impeller can be modulated or swung to make the flow of blood unsteady. To accomplish this, the three balls can be disposed individually at different distances from the rotation center axis of the impeller so that the three balls can move individually along different circular tracks. Or, instead of disposing the three balls symmetrically around the rotation center axis of the impeller, that is, equally spaced at 120° intervals around the rotation center axis of the impeller, the three balls can be disposed unsymmetrically, that is, spaced individually at different angles: 100°, 140° and 120° for example, around the rotation center axis.

The casing 3 has the inlet port 34 at the top section of the conical section 31 and also has the outlet port 35 at the cylindrical section 32 formed at the lower section of the conical section 31. At the lower section of the cylindrical section 32, the bottom plate 33 is joined watertightly. On the lower section side of the bottom plate 33, a magnet drive means 4, is mounted to support the impeller at the center of the bottom section of the casing 3 and to rotate the impeller 1 around the rotation center axis thereof in cooperation with the permanent magnets 14.

More particularly, under a rotation frame 43 (FIG. 1) or a rotation disc 43 (FIG. 5) radially extending in the horizontal direction from a rotation shaft connector 42 located at the central section, an appropriate number of permanent magnets 41, preferably the number of the permanent magnets 41 being equal to that of the permanent magnets 14, are disposed with their polarities being set opposite to those of the permanent magnets 14 so that they attract one another, and supported symmetrically around the center axis of the above-mentioned rotation shaft connector 42 to form a rotary magnet assembly. This rotary magnet assembly is provided inside a circular flange 333 projecting downward under the bottom plate 33 so that the permanent magnets 41 are disposed opposite to the permanent magnets 14 of the impeller with the bottom plate 33 intervened therebetween. Furthermore, the rotary magnet assembly is rotatably supported by a frame 44 installed at the lower end of the above-mentioned flange 333 via a bearing 45. Accordingly, the impeller 1 is supported by magnetic coupling force generated by the permanent magnets 14 provided on the bottom surface 12 of the impeller 1 and by the permanent magnets 41 disposed opposite to the permanent magnets 14 with the bottom plate 33 intervened therebetween so that the rotation center axis of the impeller 1 is positioned at the center of the bottom plate 33 of the casing 3. By connecting the rotation shaft of a rotary drive means such as a motor to the rotation shaft connector 42 and by rotating the rotary magnet assembly, the impeller 1 is rotated around the rotation center axis thereof by the coupling effect of the permanent magnets 14 and 41.

Figure 5:
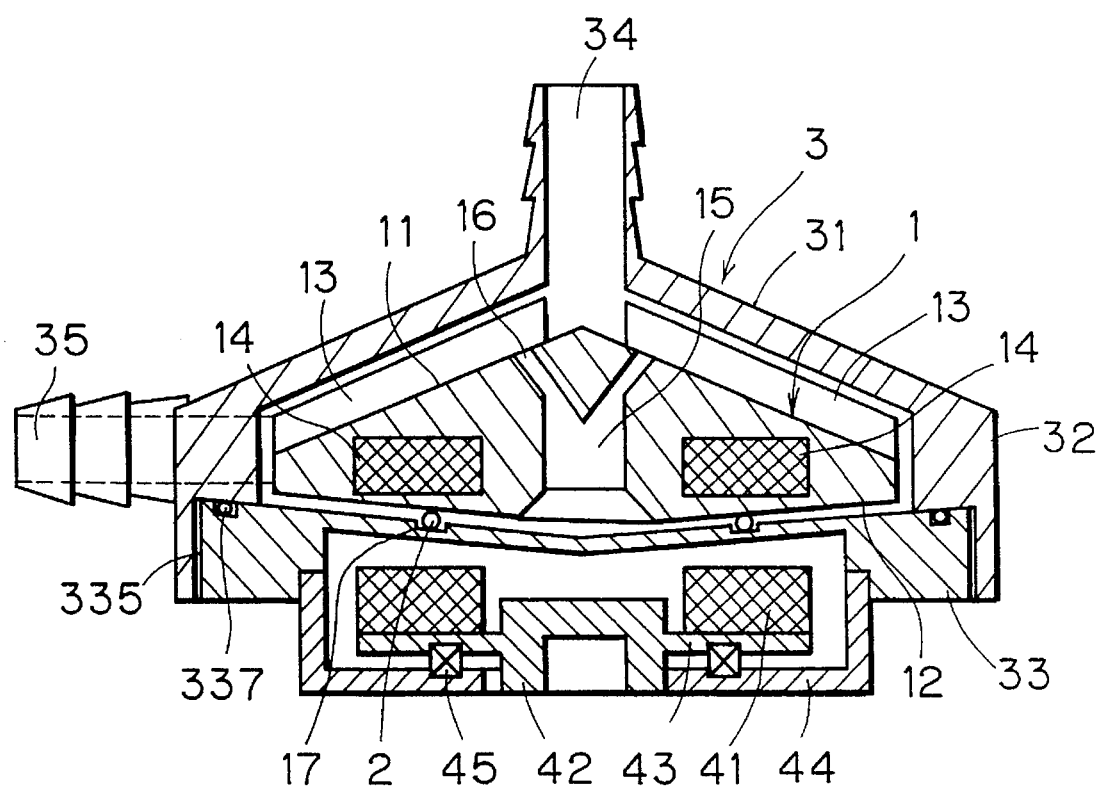
FIG. 5 is a vertical sectional view of another embodiment of the blood pump of the present invention.
Figure 6:
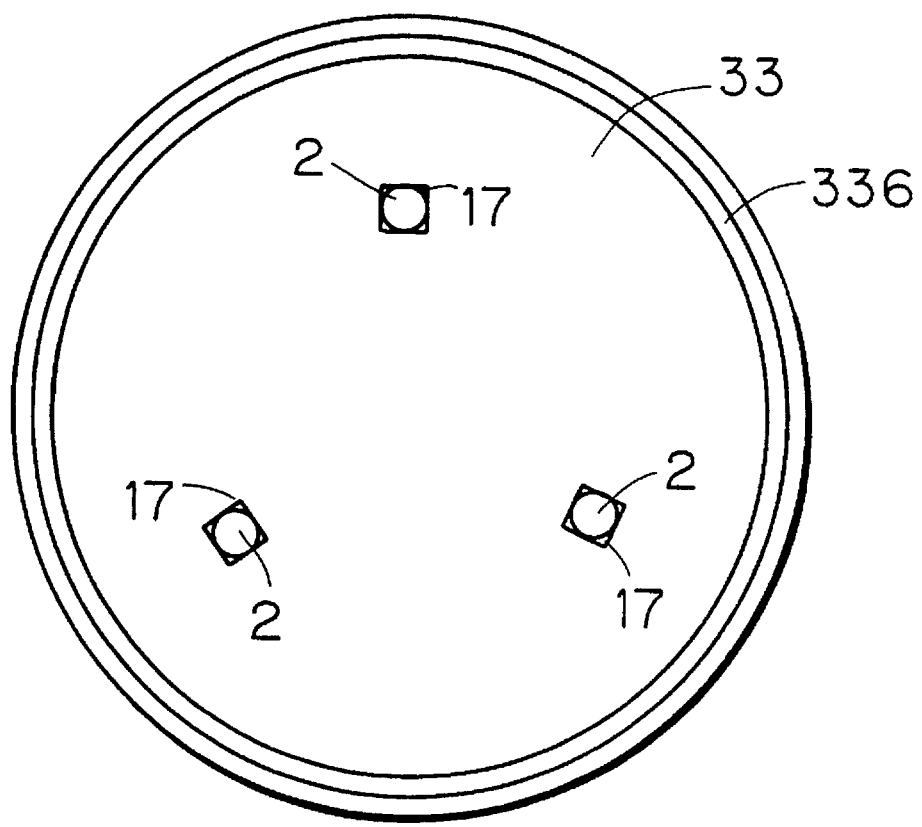
FIG. 6 is a top plan view of the bottom plate of the casing of the embodiment of the blood pump shown in FIG. 5.
Figure 7:
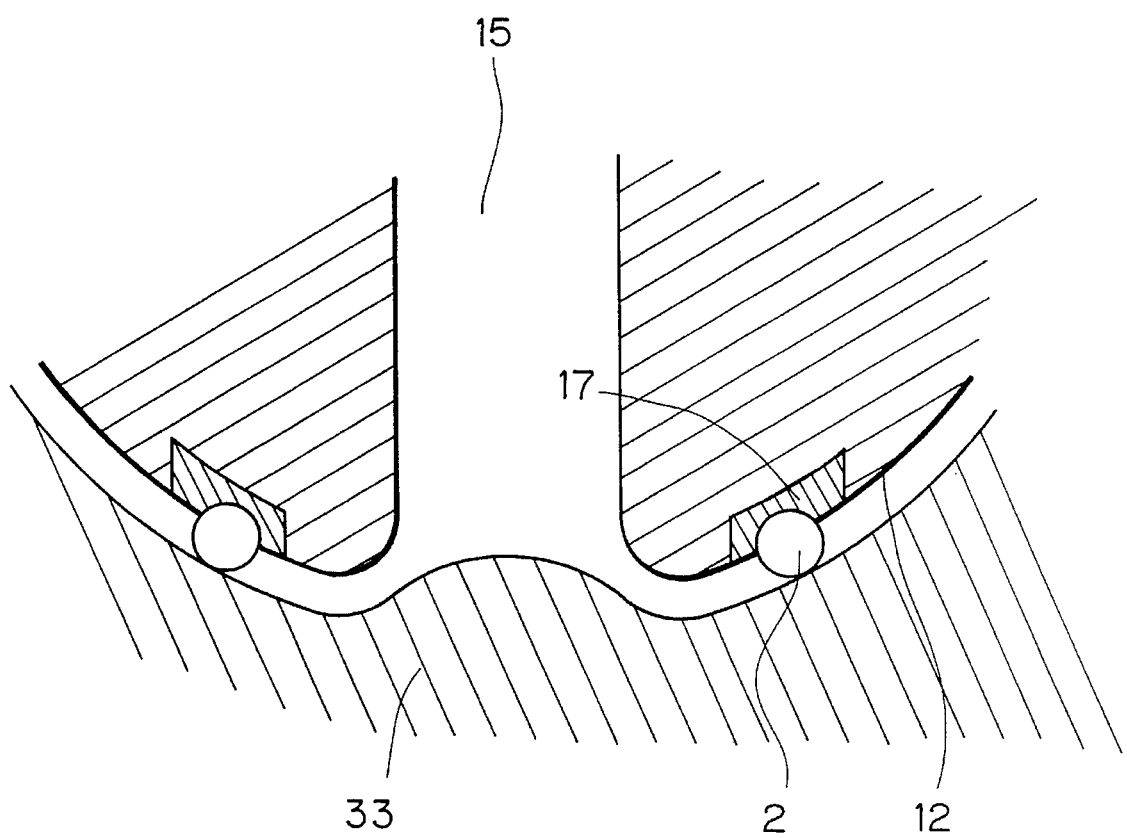
FIG. 7 is an enlarged sectional view of another embodiment of a supporting section for supporting the impeller above the bottom plate of the casing by using balls.

FIGS. 5 and 6 show another embodiment of the blood pump of the present invention. The same numerals as those used in FIGS. 1 to 3 represent the corresponding parts. In this embodiment, the ball supporting sections 17 for supporting the balls 2 which rotatably support the impeller 1 above the bottom plate 33 of the casing 3 are disposed on the bottom plate 33 of the casing 3, and the ball receiving section 331 is formed on the bottom surface 12 of the impeller so that the balls 2 roll and rotate while contacting the ball receiving section 331. In FIG. 5, the bottom surface 12 of the impeller 1 and the upper surface of the bottom plate 33 of the casing 3 are inclined to form downward conical shapes having their vertexes at the centers of the bottom and upper surfaces respectively. In this respect, FIG. 5 differs significantly from FIG. 1. By using the inclined conical side surface as a ball receiving surface on which the balls 2 roll, the balls 2 are prevented from going out of their track in the horizontal direction due to centrifugal force, thereby offering the effect of stably holding the impeller 1 at the central position above the bottom plate. This effect can also be obtained by using the above-mentioned guide groove 332. Furthermore, as shown in FIG. 7, this effect can also be obtained by providing a conical projection 334 or a spherical projection at the central section of the bottom plate 33. In all of these cases, the rotation behavior of the balls 2 along the track at the ball receiving section 331 is stabilized.

In the embodiment shown in FIGS. 5 and 6, the bottom plate 33 of the casing 3 is joined to the cylindrical section 32 via a screw 335. Numeral 336 represents an O-ring groove and numeral 337 represents an O-ring. The embodiment shown in FIGS. 5 and 6 is assembled in the almost same way as the embodiment shown in FIGS. 1 to 3, except that the permanent magnets 41 are supported on the rotation frame 43.

Figure 8:
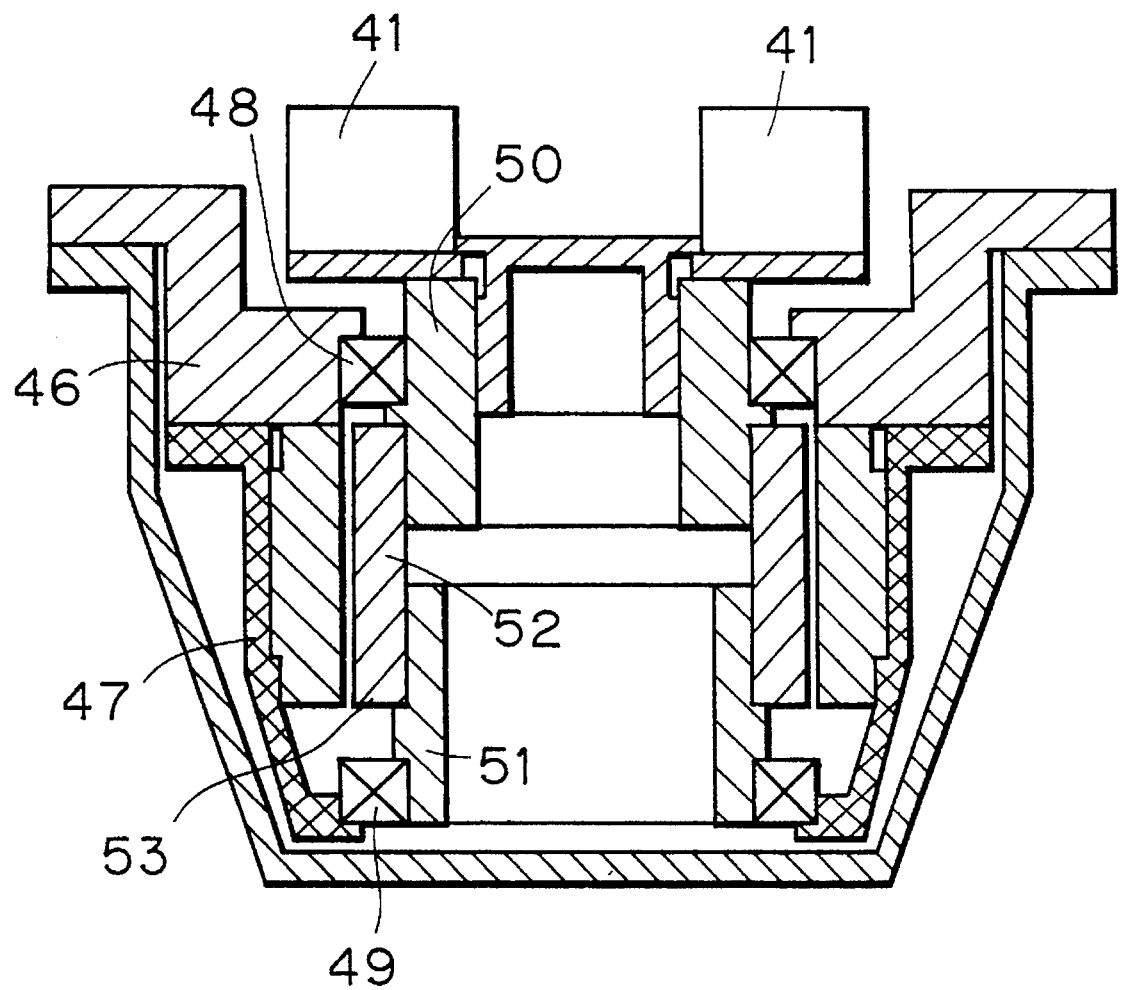
FIG. 8 is a vertical sectional view of another embodiment of a magnet drive means of the blood pump of the present invention.

FIG. 8 shows another embodiment of a magnet drive means 4 which functions as the magnet drive means. This magnet drive means 4 integrally accommodates a rotor and a stator which are used to form a motor for rotating the permanent magnets 41 so that the entire size of the magnet drive means including its drive motor is made smaller. A drive rotor 52, such as the rotor of a DC brushless motor, is installed on a notation shaft 50 supported by a frame 46 via a bearing 48 as well as on a rotation shaft 51 supported by a frame 47 via a bearing 49. The stator 53 of the drive motor is supported by the frame 47 and disposed adjacent to the outside of the rotor. The permanent magnets 41 are installed on the rotation shaft 50. This magnet drive means 4 is used in connection with the casing 3 accommodating the impeller 1, only when the pump is operated. Although the impeller 1 and casing 3 can be thrown away, the magnet drive means 4 can be used repeatedly.

The embodiments of the blood pump of the present invention described above have no pivots or shafts for supporting the impeller, no bearings for support pivots or shafts, and no supporting means for supporting bearings. With this structure, blood sucked from the inlet port 34 and discharged from the outlet port 35 by the pumping action of the pump vanes 13 due to the rotation of the impeller 1 does not collide against bearings or bearing supporting means, and the flow of the blood is not disturbed by such obstacles, thereby not causing hemolysis and thrombus. Consequently, the generation of hemolysis or thrombus during pump operation can be reduced significantly. In addition, since the impeller 1 is supported by at least three balls 2 on the bottom plate 33 of the casing 3 and the impeller 1 is held at the center of the bottom plate 33 and rotated by the cooperative operation of the permanent magnets 14 and 41, the rotation of the impeller is extremely smooth and stable, thereby enabling continuous pump operation for an extended period of time.

Figure 9:
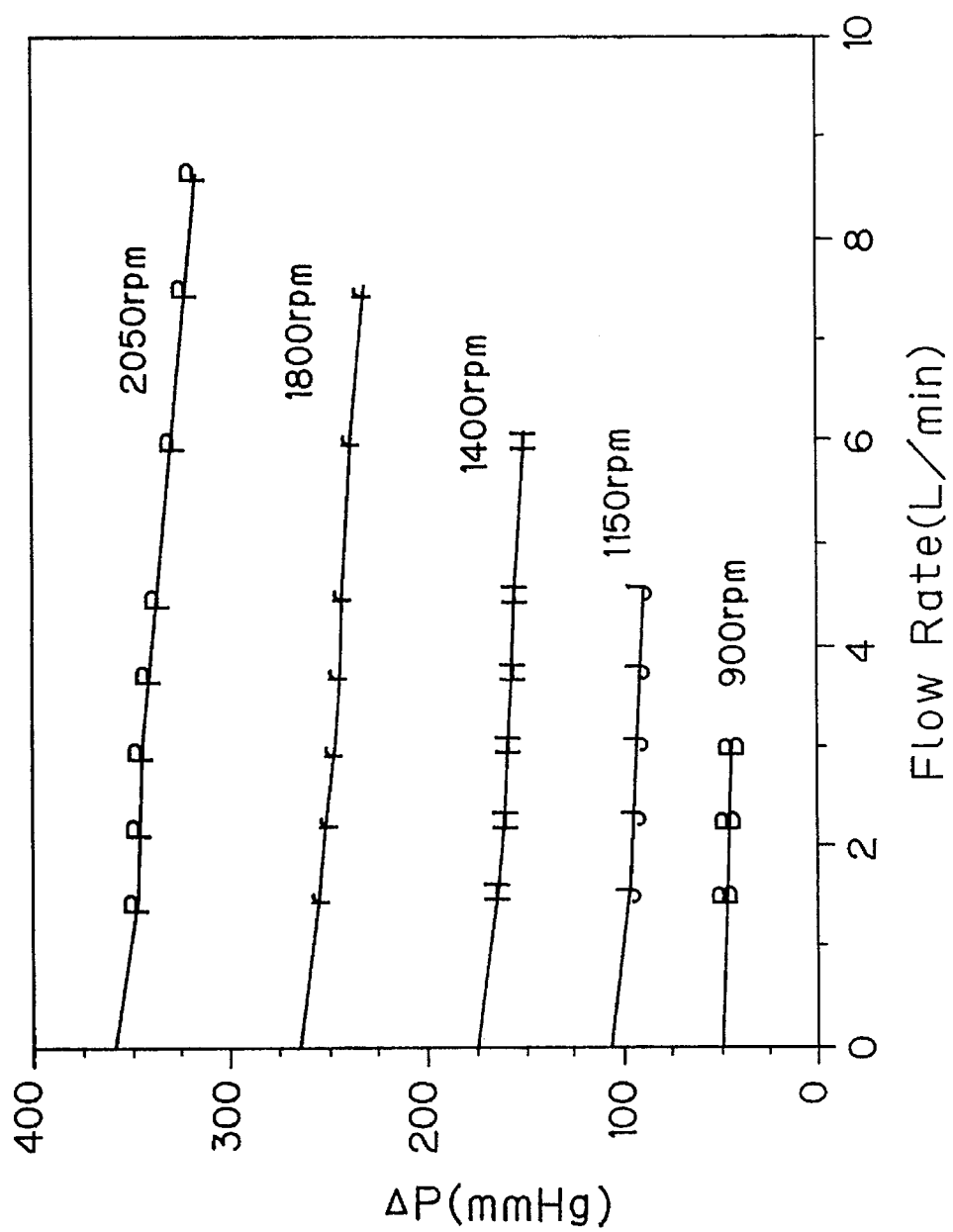
FIG. 9 is a graph illustrating the results of the performance test of the embodiment shown in FIGS. 5 and 6.

FIG. 9 shows a graph indicating the results of the performance test of the embodiment shown in FIGS. 5 and 6 when water is pumped. The ordinate of the graph represents the difference between the outlet pressure and inlet pressure, and the abscissa represents the flow rate. The results indicate that the embodiment can be used satisfactorily for heart-lung machines.

A still another embodiment of the present invention is explained next referring to FIGS. 10 and 11. The same numerals as those used in the previous figures represent the corresponding parts. The impeller of this embodiment is supported by the casing 3 via pivots 21, 23 and pivot bearings 22, 24 at both the upper and lower ends of the rotation center axis thereof. The pivot 21 formed at the lower end of the rotation shaft 19 of the impeller 1 is supported by a bearing 22, a watch-type jewelled bearing, disposed at the center of the bottom plate 33 of the casing 3. The pivot 23 formed at the upper end of the above-mentioned rotation shaft is supported by a pivot bearing 24, which is similar to the bearing 22, embeddedly disposed at the top section 311 of the conical section 31 of the casing 3. The inlet port 34 of the casing 3 extends parallel to the center line of the conical section at a position eccentric from the top section 311 of the conical section 31 of the casing 3. More particularly, the inlet port 34 is disposed so that the center axis thereof is positioned 5 mm away from the center line of the conical section of the casing in parallel to the center line. Furthermore, in this embodiment, auxiliary vanes 25 are disposed on the bottom surface 12 of the impeller 1 to prevent the generation of thrombus which is apt to occur because of the stagnation of blood around the pivot 21 and the pivot bearing 22 at the lower end of the rotation shaft 19 of the impeller 1. The generation of thrombus can be prevented more effectively by disposing water-purging through holes (not shown) around the bearing 22 provided on the bottom plate 33 of the casing 3 and by supplying mixture liquid of physiological saline solution, anticoagulant and thrombolytic agent via the through holes from outside the pump, although the through holes are not shown in the figures. Moreover, in this embodiment, the frame 44 of the magnet drive means 4 is threadedly engaged with the bottom plate 33 of the casing via a thread 54 so that the magnet drive means 4 is removably installed in the casing 3. Accordingly, although the casing 3 and the impeller 1 can be thrown away, the magnet drive means 4 can be used repeatedly.

In the two pairs of the pivots and the pivot bearings disposed at the upper and lower ends of the rotation shaft 19 of the impeller 1, at least one part of each pair should preferably be made of ceramics, such as alumina, zirconia, silicon carbide or silicon nitride, being superior in resistance against thrombus and friction.

Since both the upper and lower ends of the rotation shaft 19 of the impeller 1 used in this embodiment are supported by bearings 22, 24, the rotation of the impeller 1 is smooth and stable. In addition, since the bearing 24 of the pivot 23 is disposed in the wall of the top section of the conical section of the casing 3, no supporting means is necessary to support the bearing. Furthermore, since the inlet port 34 is disposed eccentric from the top section of the conical section as described above, blood sucked from the inlet port 34 does not directly collide against the pivot 23 and the bearing 24, and the flow of the blood is not disturbed by these parts. Consequently, in the case of this embodiment of the blood pump of the present invention, the generation of hemolysis and thrombus can also be prevented at the supporting section on the upper end side of the rotation shaft 19 of the impeller 1, thereby enabling the embodiment to be operated continuously for an extended period of time.

Figure 10:
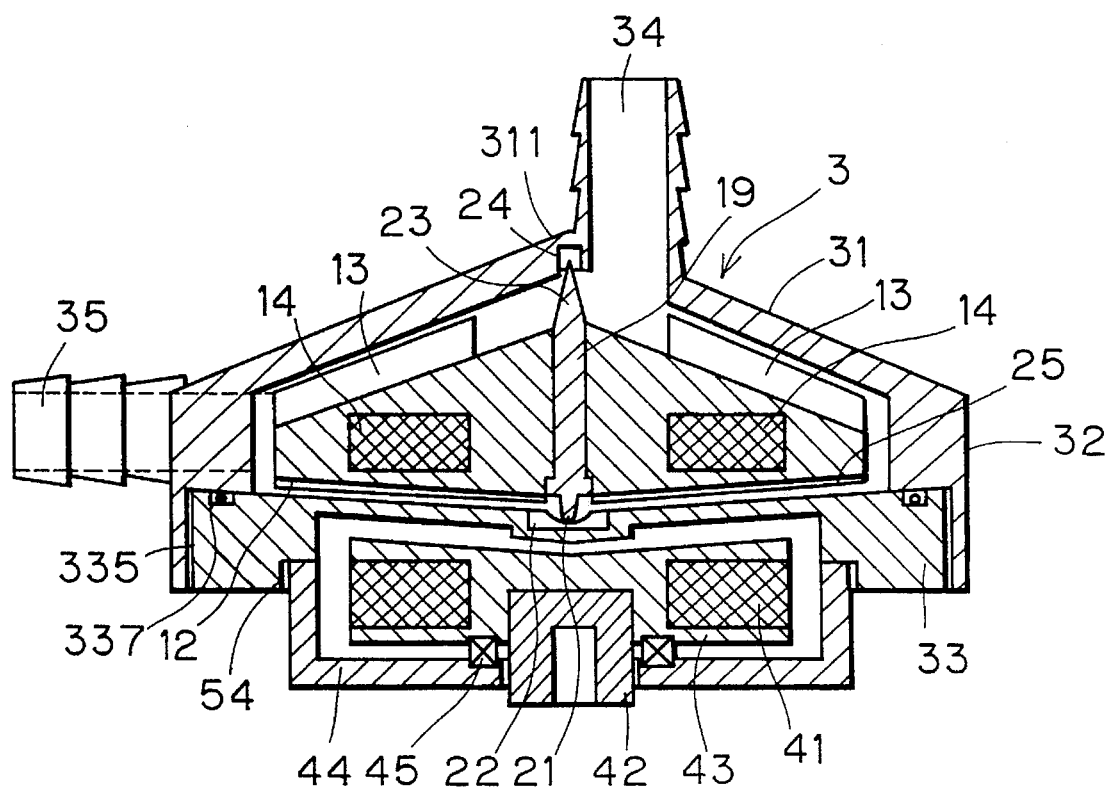
FIGS. 10 and 11 are a vertical sectional view and a top plan view respectively illustrating still another embodiment of the blood pump of the present invention.
Figure 11:
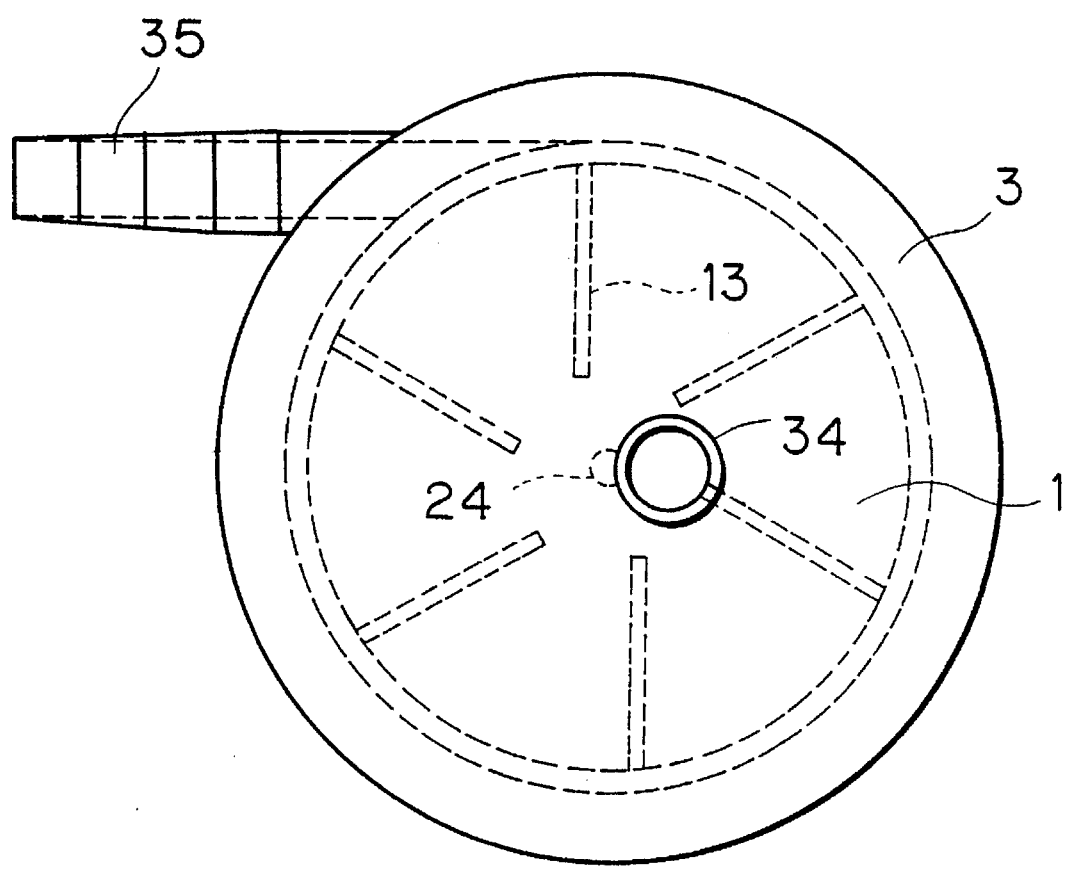
Figure 12:
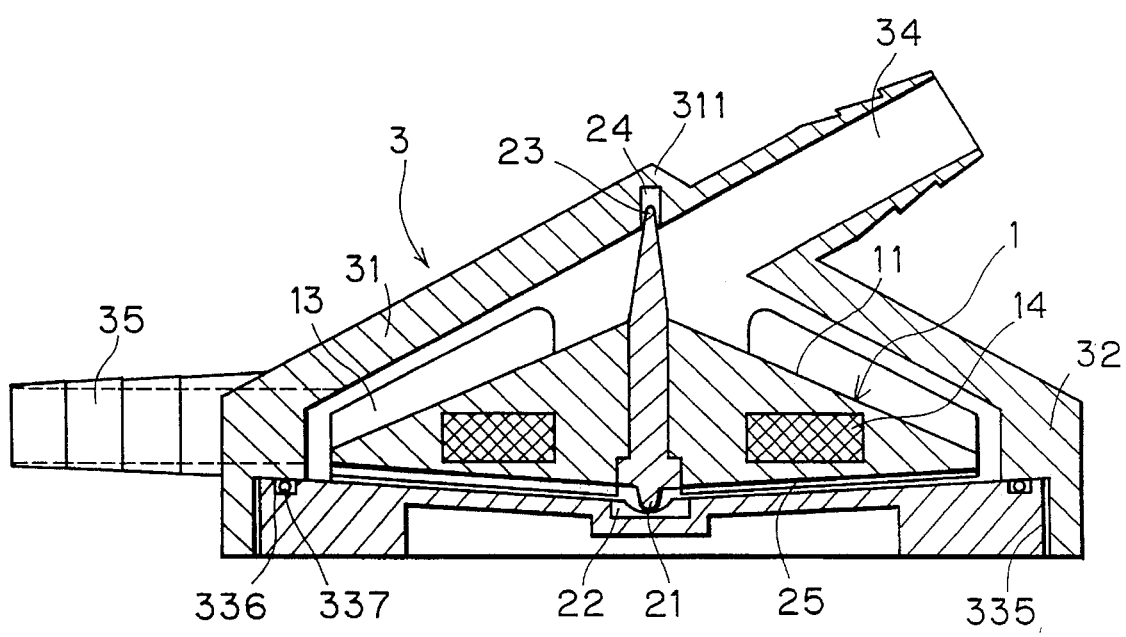
FIGS. 12 and 13 are a vertical sectional view and a top plan view respectively illustrating yet still another embodiment of the blood pump of the present invention.
Figure 13:
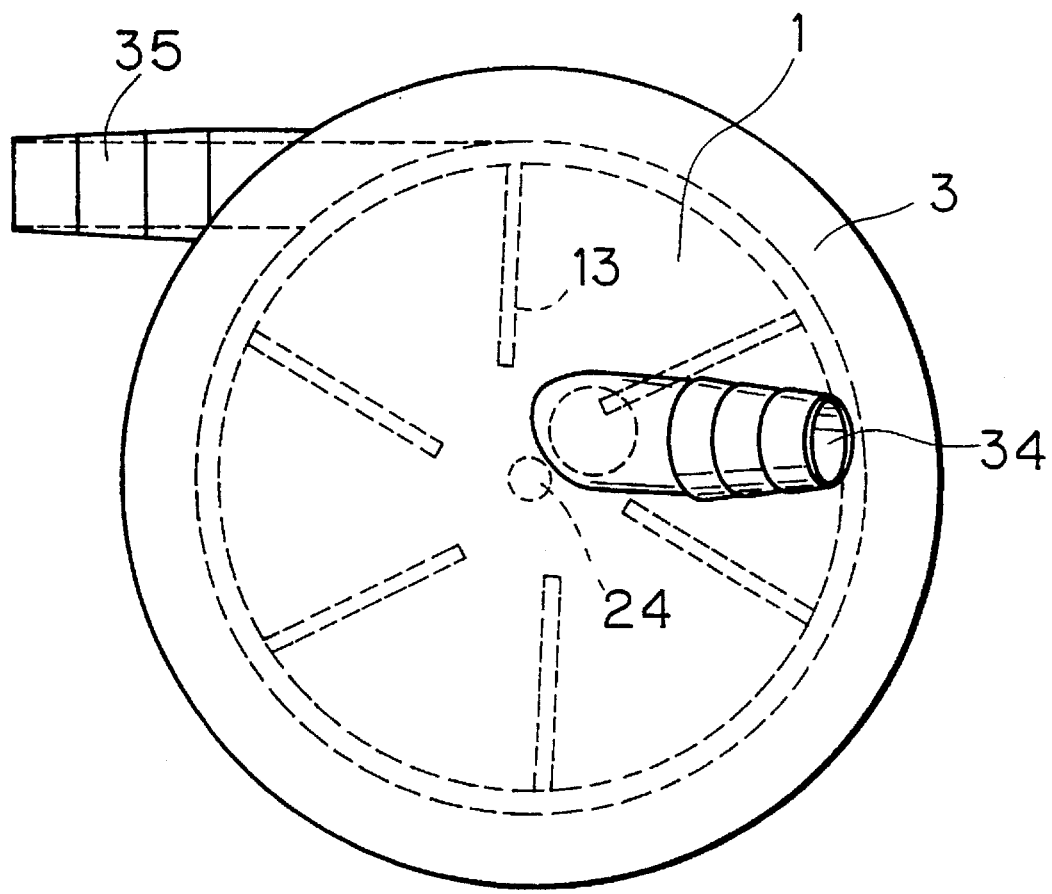

FIGS. 12 and 13 show yet another embodiment wherein the extension direction of the inlet port described in the above-mentioned embodiment shown in FIGS. 10 and 11 is changed. In this embodiment, the inlet port 34 is positioned eccentric from the top section of the conical section and extends in an inclined direction instead of the direction parallel to the center line of the conical section. Except for the inclined inlet port 34, this embodiment is the same as the embodiment of the blood pump shown in FIGS. 10 and 11. (FIGS. 12 and 13, however, show a condition wherein the magnet drive means 4 is removed.) Accordingly, in this embodiment of the blood pump of the present invention, the rotation of the impeller 1 is smooth and stable, and the generation of hemolysis and thrombus is prevented around the pivot and the pivot bearing 24 at the upper end of the rotation shaft 19 of the impeller 1. Moreover, since the angle between the inclined extension direction of the inlet port 34 and the direction of the outlet port 35 of this embodiment of the blood pump can be set at any value in the range of 360° or less, the blood pump can be embedded at any position. When this blood pump is used for external blood circulation or heart-lung machines, it is advantageous in that the pump can be easily built in a variety of circuits.

Figure 14:
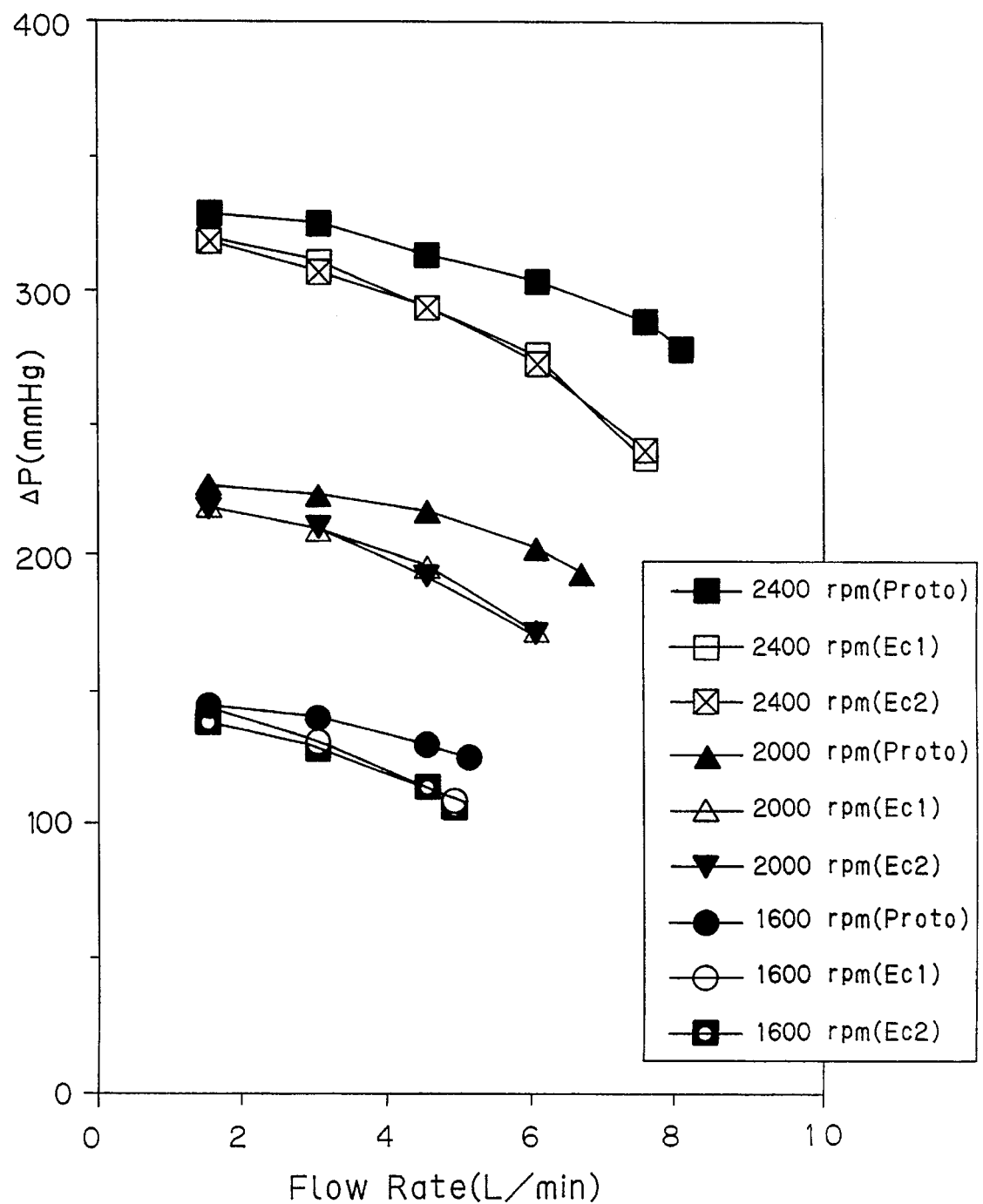
FIGS. 14 and 15 are graphs illustrating the results of the performance tests of the embodiments of the blood pump of the present invention and the above-mentioned conventional blood pump.
Figure 15:
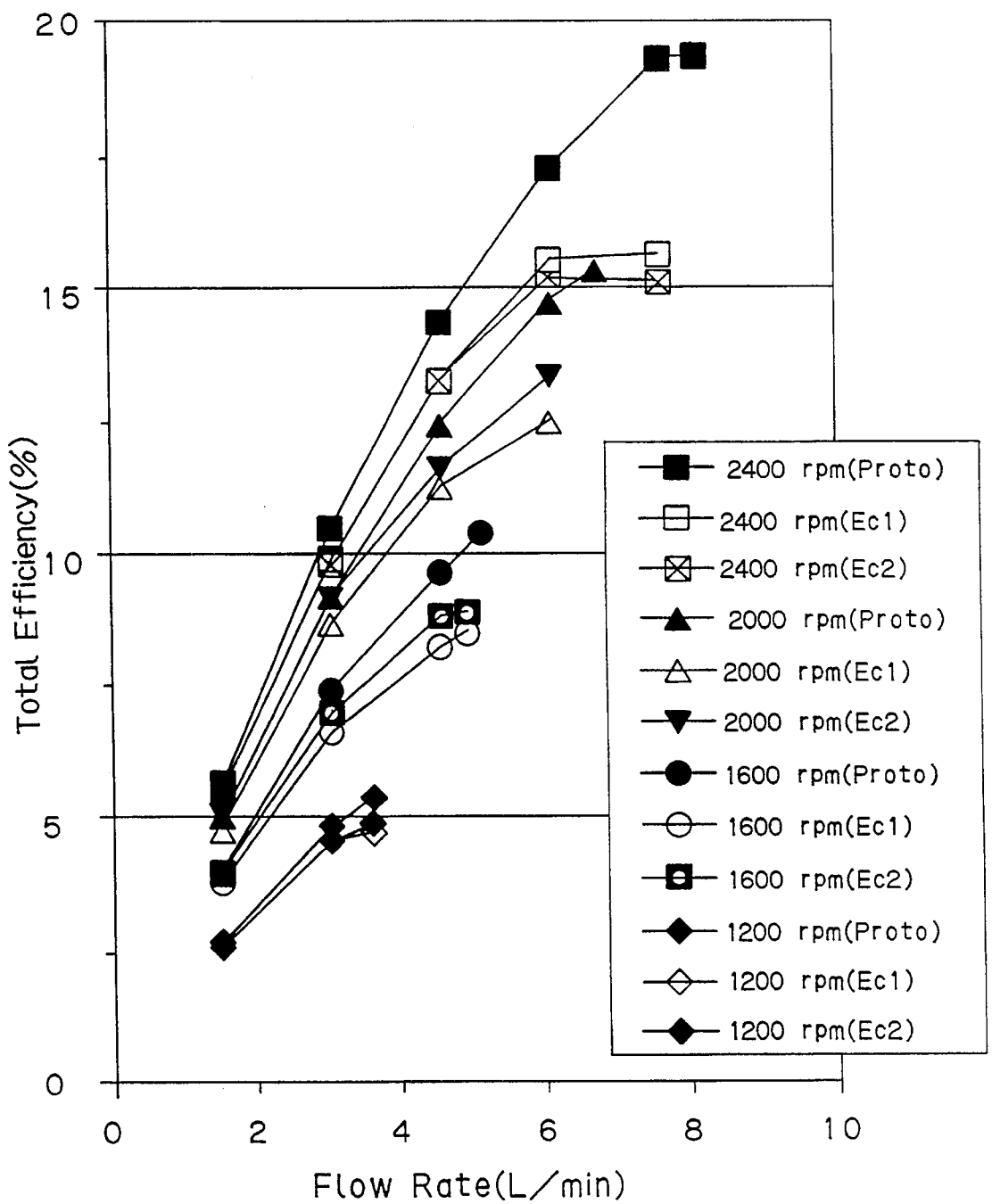

FIGS. 14 and 15 are graphs illustrating the results of the performance tests of the embodiments of the blood pump of the present invention and the above-mentioned conventional blood pump. The structure of the conventional pump used for the performance tests is almost similar to that of the pump shown in FIGS. 10 and 11, except that the inlet port is positioned at the top section of the conical section of the casing, not eccentric from the top section of the conical section and that the bearing for supporting the pivot at the upper end of the rotation shaft of the impeller is positioned just under the above-mentioned inlet port and supported by a supporting bar, thereby causing blood sucked from the inlet port to collide against the bearing and the supporting bar, and disturbing the flow of the blood, thus easily allowing the generation of hemolysis and thrombus.

Referring to the graph shown in FIG. 14, the ordinate of the graph is the pressure difference P between the outlet pressure and the inlet pressure, and the abscissa of the graph is the flow rate. Referring to the graph shown in FIG. 15, the ordinate is the total efficiency and the abscissa is the flow mate. The total efficiency is represented in percentage of hydraulic drive power per unit electric power consumption. The data indicated by Proto in the figures correspond to the conventional blood pump, the data indicated by EC1 correspond to the embodiment of the blood pump shown in FIGS. 10 and 11, and the data indicated by EC2 correspond to the embodiment of the blood pump shown in FIGS. 5 and 6. It seems that all of these blood pumps have performance suited to be used for the blood pumps of heart-lung machines.

Additionally, in the blood pumps shown in FIGS. 1 to 3 and FIGS. 5 and 6, having a structure wherein the impeller is supported by at least three balls and the bearing on the upper side is eliminated, the inlet port can be positioned eccentric from the rotation shaft of the impeller as shown in FIGS. 10 to 15. In this case, a type wherein the center axis of the inlet port is inclined from the rotation center axis of the impeller and both the axes have an intersection is effective in pump efficiency and hemolysis prevention characteristics. A blood pump having this kind of inclined inlet port is very useful as a blood pump to be embedded inside the human body.

The blood pumps of the present invention described above can be changed and modified as described below. In stead of the embodiments shown in FIGS. 10 and 11, and FIGS. 12 and 13, the shapes of the impeller and the casing can be changed so that each of them has conical sections at the top and bottom sections thereof and a cylindrical section between the top and bottom sections, and the impeller is equipped with the pump vanes in its conical bottom section and accommodates the magnet means in its cylindrical section, while the casing accommodates the magnet drive means in its cylindrical section. This structure was already presented in U.S. patent application Ser. No. 07/940,510 in FIGS. 2 and 3 by one of the co-inventors of the present application. The permanent magnets 41 of the magnet drive means can be changed to coils for generating a rotating magnetic field to eliminate a rotary drive means such as a motor used to rotate the permanent magnets 41. Moreover, only the lower end of the rotation shaft of the impeller can be supported by a pivot and a pivot bearing, the upper end side of the impeller can be supported by at least three balls under the casing, the magnet means for rotating the impeller can be disposed on the upper section side of the impeller, and the magnet drive means can be disposed on the upper side of the casing, without causing any problems.

Although centrifugal pumps are taken as examples for explanation in the above-mentioned embodiments, the present invention is also applicable to rotary pumps, such as axial flow, screw flow and mix flow pumps.

It is further understood that the characteristics of the embodiments of the blood pump of the present invention can be combined, changed and modified additionally in various ways within the spirit and scope of the present invention.

We claim:

1. A blood pump, comprising:

a casing defining an inlet, an outlet and a bottom, a substantially conical impeller rotatably accommodated in the casing, the impeller defining a side, a bottom, a rotational axis and an upper end, the side and the upper end of the impeller being unsupported by a bearing, pump vanes provided on the side of the impeller, magnet means provided on the bottom of the impeller for rotating the impeller, magnet drive means disposed opposite to the magnet means with the casing intervened therebetween for supporting the impeller above the bottom of the casing and for rotating the impeller around the rotational axis of the impeller in cooperation with the magnet means, and at least three balls above the bottom of the casing for rotatably supporting the impeller.

2. The blood pump of claim 1, comprising:

at least one ball supporting section disposed on at least one of the bottom of the impeller and the bottom of the casing for rotatably supporting at least one of the balls.

3. The blood pump of claim 1, wherein at least one of the balls comprises a ceramic material and has a diameter in the range of 1 to 10 mm.

4. The blood pump of claim 1, comprising at least one ball receiving section disposed on at least one of the bottom of the impeller and the bottom of the casing for rotatably supporting at least one of the balls, the ball receiving section defining a guide groove.

5. The blood pump of claim 1, wherein the impeller has a center stabilizing hole which communicates with an opening disposed at the central section of the bottom surface and a ring-shaped opening disposed around the top section of the impeller and extends along the rotational axis of the impeller and substantially parallel to the rotational axis.

6. The blood pump of claim 1, wherein the magnet drive means is removably disposed in the casing.

7. The blood pump of claim 1, wherein the magnet means and the magnet drive means comprise permanent magnets and the permanent magnets of the magnet drive means are rotatably installed under the bottom of the casing.

8. A blood pump, comprising:

a casing defining an inlet, an outlet and a bottom, a substantially conical impeller rotatably accommodated in the casing, the impeller defining a side, a bottom, a rotational axis and an upper end unsupported by a bearing, pump vanes provided on the side of the impeller, magnet means provided on the bottom of the impeller for rotating the impeller, magnet drive means disposed opposite to the magnet means with the casing intervened therebetween for supporting the impeller above the bottom of the casing and for rotating the impeller around the rotational axis of the impeller in cooperation with the magnet means, and at least three balls above the bottom of the casing for rotatably supporting the impeller, wherein the impeller defines at least one space substantially adjacent at least one of the ball supporting sections, the space being substantially filled with an anticoagulant.

* * * * *